(12) United States Patent
Mohindra

(10) Patent No.: US 12,364,622 B2
(45) Date of Patent: Jul. 22, 2025

(54) APPLIANCE FOR REDUCING FACIAL AGEING AND/OR ORAL PARAFUNCTIONAL ACTIVITY

(71) Applicant: Naresh Kumar Mohindra, London (GB)

(72) Inventor: Naresh Kumar Mohindra, London (GB)

(*) Notice: Subject to any disclaimer, the term of this patent is extended or adjusted under 35 U.S.C. 154(b) by 0 days.

(21) Appl. No.: 17/207,332

(22) Filed: Mar. 19, 2021

(65) Prior Publication Data

US 2021/0307955 A1 Oct. 7, 2021

Related U.S. Application Data

(63) Continuation of application No. 14/910,196, filed as application No. PCT/GB2014/052359 on Jul. 31, 2014, now abandoned.

(30) Foreign Application Priority Data

Aug. 6, 2013 (GB) ...................................... 1314053

(51) Int. Cl.
| | | |
|---|---|---|
| *A61F 5/56* | (2006.01) | |
| *A61C 7/08* | (2006.01) | |
| *A63B 71/08* | (2006.01) | |

(52) U.S. Cl.
CPC ............... *A61F 5/566* (2013.01); *A61C 7/08* (2013.01); *A61F 2005/563* (2013.01); *A63B 71/085* (2013.01)

(58) Field of Classification Search
CPC ...... A61F 5/566; A61F 2005/563; A61F 5/56; A63B 71/085; A63B 2071/086;
(Continued)

(56) References Cited

U.S. PATENT DOCUMENTS 5,235,991 A 8/1993 Minneman
5,299,936 A 4/1994 Ueno
(Continued)

FOREIGN PATENT DOCUMENTS

WO WO 2003/105716 A1 12/2003

OTHER PUBLICATIONS

Hardy, L. (Oct. 12, 2009). Can this little bit of plastic make you look ten years younger? Retrieved Jan. 19, 2019, from https://www.dailymail.co.uk/femail/beauty/article-1217316/Can-little-bit-plastic-make-look-years-younger.html; pp. 1-7. (Year: 2009).*

(Continued)

*Primary Examiner* — Rachael E Bredefeld
*Assistant Examiner* — Seth R. Brown
(74) *Attorney, Agent, or Firm* — Klarquist Sparkman, LLP

(57) ABSTRACT

An appliance for use in a method of reducing facial aging and/or oral parafunctional activity comprising two parts, each comprising a composite structure comprising: a first layer formed of a durable, resilient, elastomeric material comprising a cured thermoset rubber and which in use contacts the occlusal biting surfaces of the posterior teeth; and a second layer formed of a durable, non-deformable material having a softening point over 100° C. which provides a bite plate; wherein the second layer of each part is provided with a protrusion formed of durable, non-deformable material having a softening point over 100° C. which is positioned such that in use the protrusion extends from the surface above at least a part of the first and/or second molar teeth which are in contact with the first layer. A method of making the appliance, a kit of parts, and methods of use are also disclosed.

19 Claims, 2 Drawing Sheets

(58) Field of Classification Search
CPC ....... A63B 2071/088; A61C 7/36; A61C 7/08;
A61C 9/00; A61C 9/006; A61C 9/0006;
A61M 16/0488; A61M 16/049; A61M
16/0493; A61M 2025/022; A61B 90/16
USPC ........................................ 128/859, 861, 862
See application file for complete search history.

(56) References Cited

U.S. PATENT DOCUMENTS

| | | | |
|---|---|---|---|
| 5,879,155 A | 3/1999 | Kittelsen | |
| 5,884,628 A * | 3/1999 | Hilsen | A61F 5/566 128/859 |
| 6,092,523 A | 7/2000 | Belfer | |
| 6,371,758 B1 | 4/2002 | Kittelsen | |
| 6,415,794 B1 | 7/2002 | Kittelsen et al. | |
| 6,539,943 B1 | 4/2003 | Kittelsen et al. | |
| 7,416,516 B2 * | 8/2008 | Mohindra | A61C 7/08 128/859 |
| 8,419,595 B1 | 4/2013 | Hanswirth et al. | |
| 8,453,650 B1 * | 6/2013 | Frey | A61F 5/56 128/862 |
| 2009/0087812 A1 | 4/2009 | Andersen | |
| 2011/0174319 A1 | 7/2011 | Busciglio | |
| 2016/0175138 A1 | 6/2016 | Mohindra | |

OTHER PUBLICATIONS

Polyvinyl siloxane, Wikipedia, https://en.wikipedia.org/wiki/Polyvinyl_siloxane (Year: 2020).*
Hardy, L. (Oct. 12, 2009). Can this little bit of plastic make you look ten years younger? from https://www.dailymail.co.uk/femail/beauty/article-1217316/Can-little-bit-plastic-make-look-years-younger.html; pp. 1-7. (Year: 2009).*
Hardy, "Can this little bit of plastic make you look ten years younger?," retrieved Jan. 19, 2019 from https:/www.dailymail.co.uk/femail/beauty/article-1217316/Can-little-bit-plastic-make-look-years-younger.html, pp. 1-7, 2009.
Mohindra and Bulman, "The Effect of Increasing Vertical Dimension of Occlusion on Facial Aesthetics," *British Dental Journal* 192:164-169, 2002.
Mohindra, "A Preliminary Report on the Determination of the Vertical Dimension of Occlusion Using the Principle of the Mandibular Position in Swallowing"; *British Dental Journal* 180:344-348, 1996 (Abstract).
Mohindra, "A Preliminary Report on the Determination of the Vertical Dimension of Occlusion Using the Principle of the Mandibular Position in Swallowing," *British Dental Journal* 180:344-348, 1996.
Wikipedia, Polyvinyl Siloxane, 2020.
Written Opinion and International Search Report International Application No. PCT/GB2014/052359, dated Oct. 31, 2014 (12 pages).

* cited by examiner

APPLIANCE FOR REDUCING FACIAL AGEING AND/OR ORAL PARAFUNCTIONAL ACTIVITY

CROSS REFERENCE TO RELATED APPLICATIONS

This is application is a continuation of U.S. application Ser. No. 14/910,196, filed Feb. 4, 2016, which is the U.S. national stage of PCT/GB2014/052359, filed Jul. 31, 2014, which claims priority from United Kingdom Application No. 13140153.8, filed Aug. 6, 2013.

FIELD

This invention is concerned with an appliance which is intended to be worn in the mouth and which, over time, can lead to a reduction in facial aging and/or reducing of oral parafunctional activity, preferably bruxism.

BACKGROUND

Pivot appliances have been used in dentistry since the 1930s to alleviate pain experienced by patients suffering from misaligned jaws, caused by inclines of the teeth. The original purpose of the pivot appliance was to separate the jaws so that inclines of the teeth would not dictate how the jaws met and thereby allow the bite of the patient to be adjusted to a more comfortable position. Use of the appliance on a temporary basis would allow the facial muscles to relax, resulting in the jaw and the condyle in the temporo mandibular joint (tmj) resting in an unrestrained position. This consequently would result in relief of pain associated with the tmj disorder.

The pivot appliance was made from a plaster mould of the patient's mouth, which mould was made by taking an impression of the lower teeth with a dental impression material. From this impression, a mould was made in plaster, which was an exact duplicate of the patient's lower jaw. This mould was then used to make a pivot appliance from a rigid moulding material, which would include wire clips to fit the appliance in the patient's mouth. The optimal thickness of the moulding material of the appliance that provided the biting surface was determined e.g. by using the command swallowing technique to establish the correct biting position for the particular patient. The patient would wear the fitted appliance under the direction and supervision of a dentist for such time until relief of pain was achieved. The appliance was then removed. The problem with this temporary procedure was that it sometimes tended to provide only temporary relief: after the appliance had been removed, there was a tendency for the jaws to return over time back to their original, painful biting position.

Some dentists would advocate that the bite of the patient had to be permanently altered to achieve permanent relief from tmj disorder. In such circumstances, orthodontic treatment was usually employed, to change the position of the teeth or by crowning the teeth.

In 1996, Dr N. K. Mohindra published a paper, in the British Dental Journal, entitled "A preliminary report on determining the vertical height of occlusion by the position of the mandible in the swallowing technique". In this paper, Dr Mohindra reported that a pivotal appliance could be used to increase the vertical dimension significantly, e.g. by up to 19 mm, beyond the normal resting position of the mandible without patients experiencing problems. Prior to this report, doctors and dentists had considered that the vertical dimension should not be increased by more than about 2-3 mm and definitely not beyond the resting position of the jaw. The appliance used in these experiments was made in a laboratory by a trained and approved dental technician.

In 2002, Dr Mohindra published a second paper in the British Dental Journal, entitled "The effect of increasing vertical dimension on facial aesthetics". In this paper, Dr Mohindra reported that 80% of patients whose vertical dimension had been increased permanently by the use of a pivot appliance thought they looked between 5 and 20 years younger, and that these views were backed up by an independent panel who studied before and after photographs of the patients and reached same conclusions.

Subsequently, Dr Mohindra developed a facial rejuvenator which improved facial aesthetics without permanently increasing vertical dimension of occlusion. The rejuvenator, like the earlier dental appliance, required to be custom made for each patient in a laboratory by a trained dental technician. The rejuvenator comprised a substantially U-shaped layer formed from a durable, non-deformable material having a softening point over 100° C. which was custom moulded to fit over all the teeth on the lower jaw and which in use provided a bite plate. Two projections extended from the surface of the bite plate and were positioned on the bite plate over at least a part of the first molar tooth on both sides of the jaw. The projections were made of a durable, non-deformable material having a softening point over 50° C., and were custom moulded to the vertical height of occlusion for each patient, as determined by the command swallowing technique. The rejuvenator was removable and so only increases the vertical dimension of occlusion for the short period of time when the appliance is in the mouth of the patient. The rejuvenator was based on the original pivot appliance and is made in the same way, i.e. in a laboratory by a trained and approved dental technician.

U.S. Pat. Nos. 6,415,794 and 6,539,943 disclose a dental appliance for use by athletes during periods of exertion. The appliance consists of an occlusal posterior pad made of quadruple composite material comprising four layers of distinct materials, further comprising a first layer of a durable, resilient material, a second layer of non-softenable, flexible material, a third layer of a hard, very durable material, and a fourth layer of softenable material, engageable with the occlusal surfaces to space apart the upper and lower teeth, to absorb shock and clenching stress. An adjustable arch adapted to expand and contract to be moulded to the palate is provided connecting the posterior pads together with the mouth and out of the way of the tongue to maintain the position of the occlusal posterior pads within the mouth during use and to prevent loss of the pads such as by swallowing. The appliance may be fitted using a boil and bite technique, for example by a doctor or dentist, with no requirement for customized laboratory moulding processes.

U.S. Pat. No. 6,092,523 discloses an anti-snoring device having a dental overlay portion and a guide ramp portion slidably mounted in the dental portion. The device may be fitted using a boil and bite technique, for example by a doctor or dentist, with no requirement for customized laboratory moulding processes.

WO-A-03105716 discloses a mass produced universal dental appliance suitable for use in a method of reducing facial aging, which appliance comprises two parts, the parts intended in use to contact the posterior teeth on respective opposite sides of either the upper or lower jaw, each part comprising a composite structure comprising:

i) a first layer formed of a durable, resilient, elastomeric material having a softening point in the range from 35 to 100° C. and which in use contacts and grips the occlusal biting surfaces of the posterior teeth; and ii) a second layer formed from a durable, non-deformable material having a softening point over 100° C. and which in use provides a bite plate;

wherein the second layer of each part is provided with a protrusion, formed of durable, non-deformable material having a softening point over 100° C., which extends from at least 2 mm up to 20 mm from the surface of the bite plate away from the first layer and which is positioned such that in use the protrusion extends from the surface of the bite plate above at least a part of the first and/or second molar teeth which are in contact with the first layer. The material used to form the first layer is mouldable when placed in water at or close to boiling temperatures. The appliance can be fitted to a patient by initially heating the appliance in a microwave oven or by submerging it in near boiling water for about 30 seconds, or such other time, so as to render the material of the first layer mouldable. The patient is required to open the mouth and the appliance is then placed over the teeth on the patient's lower jaw, with the first layer in contact with the teeth and the two projections positioned over both first molar teeth. The patient is then required to gently raise the lower jaw until the teeth on the upper jaw contact the top of the projections. The patient then closes their lips and swallows. The pressure applied to the appliance by swallowing causes the material of the first layer to deform and mould itself to the shape of the teeth on the lower jaw. The appliance can then be carefully removed from the mouth of the patient and submerged in cold water to accelerate the cooling of the appliance to ambient. Once the appliance has cooled, any excess of the first layer material can be trimmed away until it forms a comfortable fit. Whilst most patients have not suffered any problems during the fitting process, some patients, particularly those that have fitted the appliance themselves without the assistance of a doctor or dentist, have expressed discomfort or even scalding in the mouth caused by the heat of the appliance when moulding the hot first layer around the teeth (this appears to be particularly the case when the patient has used a microwave oven to heat the appliance and deviated from the "boil and bite" fitting instructions provided with the appliance before inserting the hot appliance in the mouth).

U.S. Pat. No. 8,419,595 discloses a dental appliance for reducing the effect of facial aging, which is fitted using the boil and bite technique. This appliance comprises a bite plate having a continuous bottom wall and continuous inner and outer walls that extend upwardly from the side edges of the bottom wall and are generally perpendicular to the bottom wall.

US2009/0087812 discloses a self-customizable dental treatment tray in which a curable elastic material, which may be a silicone-based denture relining material, is employed as a substitute for a "boil and bite" material. The tray is profiled such that, together with the curable elastic material, upon curing the resulting dental treatment tray is customized to accurately fit on and conform to the teeth. Such customization assists in retaining the dental treatment tray on the teeth and increase the likelihood that the dental tray will precisely match the person's unique dentition. This is important if, for example, the teeth are to be treated with a bleaching agent, or other dental agent, where all exposed surfaces of the teeth must come into contact with the agent to be treated. However, the tray is unsuitable for frequent use, as the precise matching of the elastic material to the teeth makes it difficult to easily fit and remove without damaging the material.

SUMMARY

Although patients that follow the strict instructions for fitting the universal appliance have not reported problems of discomfort or scalding, the object of the present invention is to provide an appliance for reducing facial aging that does not suffer from the potential problems caused during fitting of the known universal appliance and which is suitable for frequent use associated with methods of reducing facial aging.

The present invention, in its various aspects, is as set out in the accompanying claims.

In a first aspect, the present invention provides an appliance for use in a method of reducing facial aging and/or reducing oral parafunctional activity, which appliance comprises two parts, the parts intended in use to contact the first and/or second molar teeth on respective opposite sides of either the upper or lower jaw, each part comprising a composite structure comprising:

i) a first layer formed of a durable, resilient, elastomeric material and which in use contacts at least the occlusal biting surfaces of the first and/or second molar teeth; and ii) a second layer, comprising a first surface that faces towards and contacts said first layer, a second surface that faces away from said first layer and one or more side walls that define the borders of said first and second surfaces, formed from a durable, non-deformable material having a softening point over 100° C. and which in use provides a bite plate;

wherein the second layer of each part is provided with a protrusion, formed of durable, non-deformable material having a softening point over 100° C., which extends from at least 2 mm up to 20 mm from the surface of the second surface away from the first layer and which is positioned such that in use the protrusion extends from the second surface away from at least a part of the first and/or second molar teeth which are in contact with the first layer, and wherein the second layer of each part is optionally provided with a plurality of orifices and/or projections into which or around which the first layer is moulded to secure it to the second layer;

characterized in that said durable, resilient, elastomeric material is an ambient-temperature-cured, thermoset rubber composition;

said first surface of said second layer is substantially planar; and said second layer is free of any side walls that border said first surface and that extend from said first surface in a direction away from said second surface.

In a second aspect, the present invention provides a method for making the appliance of the above first aspect, which method comprises:

i) providing an appliance-preform comprising two parts, each part comprising a said second layer as defined above; and ii) providing an uncured rubber composition which at ambient temperature cures to form a cured thermoset rubber composition that is a durable, resilient, elastomeric material;

characterized in that said method further comprises:
iii) applying said uncured rubber composition on to said first surface of each of said second layer;
iv) moulding the uncured rubber composition into the required shape, including moulding said uncured rubber into or around said plurality of orifices and/or projections when said plurality of orifices and/or projections are present, on said second layer; and
v) curing said moulded uncured rubber composition.

It will be appreciated by the skilled reader that in this aspect the cured thermoset rubber composition, which becomes attached to said second layer as the uncured rubber composition cures, forms the first layer of the composite structure of each of the two parts of the dental appliance. Attachment of the first layer may be improved when the second layer is provided with a plurality of orifices and/or projections and the uncured rubber composition is moulded into or around them during formation of the first layer. It will also be appreciated by the skilled reader that in this aspect the moulding of the uncured rubber composition into the required shape comprises moulding said uncured rubber composition around the required teeth of a patient.

In a third aspect, the present invention provides a kit of parts suitable for making the appliance of the above first aspect, characterized in that said kit comprises:
a) an appliance-preform comprising two parts, each part comprising a said second layer as defined above; and
b) i) an uncured rubber which at ambient temperature cures to form a cured silicone rubber that is a durable, resilient, elastomeric material; or
ii) a multipack composition comprising at least two components that when mixed together form an uncured rubber which at ambient temperature cures to form a cured thermoset rubber that is a durable, resilient, elastomeric material.

The kit of parts preferably comprises instructions for making an appliance of the first aspect by the method of the second aspect using the components of the kit of the third aspect.

Preferably, the cured rubber composition comprises a cured silicone rubber and optionally one or more other ingredients selected from the group comprising one or more of preservatives, pigments, rheology modifiers, dyes and fillers.

Preferably, the uncured rubber composition comprises an uncured silicone rubber and optionally one or more other ingredients selected from the group comprising one or more of preservatives, pigments, rheology modifiers, dyes and fillers.

When the uncured rubber composition is being applied to the surface of the second layer it preferably has a viscosity of at least 70 Pa·s (70,000 centipoises (cps)), more preferably at least 100 Pa·s (100,000 cps), and even more preferably at least 250 Pa·s (250,000 cps).

When the uncured rubber composition is being moulded to the required shape, it preferably has a viscosity of at least 100 Pa·s (100,000 cps), and more preferably at least 250 Pa·s (250,000 cps).

The uncured rubber composition cures at ambient temperature. The curing reaction that takes place does not lead to the temperature of the rubber composition increasing to a temperature that causes the patient to feel any discomfort during fitting of the appliance (i.e. during the moulding step iv), the moulding of the composition around the required teeth of the patient). Preferably, the temperature of the composition during curing is not above 50° C., more preferably not above 40° C. Thus, even though the rubber composition may feel warm to the patient during fitting, the patient is never exposed to any temperature that would cause discomfort or scalding in the mouth.

Uncured rubber compositions, which at ambient temperature cure to form a cured thermoset rubber composition that is a durable, resilient, elastomeric material, and multipack compositions for making said uncured rubber compositions, that are useful in the practice of the present invention and/or may be readily modified to enable them to be used in the practice of the invention are commercially available and very well known in the dentistry field. Such rubbers are typically promoted and sold as "denture reliners". For example, PermaSoft™ and ProSoft™ denture reliners available from Perma Laboratories, USA, DOC Reline-It™ denture reliner available from Majestic Drug Co., Inc, USA, Acryline™ denture reliner available from Lee Pharmaceuticals, USA, and Mucopren™ Soft Reline Material from Kettenbach LP, USA. Useful uncured rubber compositions may comprise, in addition to the uncured rubber, one or more of preservatives, pigments, rheology modifiers, dyes and fillers.

Preferably, the uncured rubber composition comprises an uncured silicone rubber. Suitable, medically acceptable uncured silicone rubbers are well known in the dentistry field, as is evident from the preceding paragraph.

As will be appreciated by those skilled in the art, the uncured rubber composition may require exposure to the atmosphere before it will cure at ambient temperature.

The uncured rubber composition may be provided in the kit of the present invention either as a single pack composition (as in feature b) i) above), or as a multipack composition (as in feature b) ii) above). Examples of a single pack composition include an uncured rubber composition contained in a syringe arrangement (in a similar syringe arrangement as a silicone bath sealant may be provided) or in a blister pack (as Mucopren™ Soft Reline Material from Kettenbach LP, USA described above).

In an appliance of the first aspect of the present invention, the first surface of the second layer is substantially planar and the second layer is free of any side walls that border said first surface and extend from said first surface in a direction away from said second surface. This is particularly advantageous as the absence of such walls enables the rubber composition to be moulded over the whole of the occlusal surfaces of the teeth and only over a portion, but not all, of the other outside surfaces of the teeth exposed in the mouth. In this way, either because the first layer tends to fit over only a portion not all of the teeth or because there are no walls that restrict movement of the first layer around the teeth, the appliance can be removed relatively easily from the mouth after use, which prolongs the useable lifetime of the appliance. In contrast, where dental trays are provided with walls, such as in US2009/0087812, and the rubber composition tends to get moulded around all outside surfaces of the teeth, the appliance tends to grip the teeth more, so requiring more effort to remove after use, with a consequential increase in the likelihood of the appliance being damaged.

An "appliance-preform" as used herein consists of the appliance of the first aspect but excluding a first layer.

As with the universal appliance disclosed in WO-A-03105716, the appliance of the present invention is adapted to provide a predetermined vertical separation of the jaws determined by the command swallowing technique and, advantageously, can be either fitted by e.g. a doctor or dentist without requiring use of customized laboratory processes or a dental technician, or it may be purchased over-the-counter and fitted by the individual user. The appliance is intended to be used by a patient to reduce the signs of facial aging and/or reduce oral parafunctional activity, particularly bruxism. The appliance advantageously does not have to be made individually for a patient, unlike the rejuvenator.

In one method of reducing facial aging and/or reducing oral parafunctional activity, the appliance of the first aspect may be worn at any time of the day, when the patient is awake or asleep. Preferably, the appliance is worn during eating or during sleeping. Use of the appliance will be generally prescribed by a doctor or a dentist or, in the case of an over-the-counter purchase, as prescribed on the accompanying instructions for use. The appliance is preferably worn for from about 3 to about 12 hours in any day. It is recommended not to wear the appliance for 24 hours of the day. The appliance is preferably used over a continuous period of from 4 to 10 weeks, typically 6 weeks, with a preferred interval before reuse of from 3 to 6 months e.g. 4 months.

In another method of reducing facial aging and/or reducing oral parafunctional activity, at least initially, the appliance is worn by the patient for up to only 1 hour, twice a day, every third day (i.e. not every day or every other day) and not at night time and not for eating. The state of each patients muscles can vary (some are very tense and some are relaxed), therefore if the patient suffers from any adverse symptoms e.g. pain from facial muscles, he/she must reduce the time they are wearing the appliance. Some patients may only be able to wear the appliance for only a few minutes at a time to start with but as the muscles become more relaxed they can start wearing it for longer periods.

The appliance of the present invention is shaped to fit over at least the biting surfaces, i.e. the occlusal surfaces, of the posterior teeth of the upper or lower jaw, preferably the lower jaw. In one embodiment, the appliance is substantially U-shaped, so as to fit comfortably over both the anterior and posterior teeth. Preferably, however, the appliance comprises two separate portions which fit over only the posterior teeth on either side of the respective jaw, with a bridging means, preferably made of either plastic or stainless steel, to connect the two portions.

Each part of the two parts of the appliance of the present invention which fit over the posterior teeth on both sides of the upper or lower jaw consists of a composite structure comprising
  i) a first layer formed a durable, resilient, elastomeric, thermoset rubber material and which in use contacts and grips the occlusal biting surfaces of the posterior teeth; and
  ii) a second layer formed from a durable, non-deformable material having a softening point over 100° C. and which in use provides a bite plate.

The second layer is provided with a protrusion formed of durable, non-deformable material having a softening point over 100° C. which extends from at least about 2 mm up to about 20 mm, preferably from about 5 mm up to about 15 mm, most preferably from about 7 mm to about 10 mm e.g. 9 mm, from the second surface of the second layer away from the first layer. The protrusion is positioned on the second layer such that in use it is over at least a part of the first and/or second molar teeth which are in contact with the first layer. When the appliance is fitted to the teeth on the lower jaw, the protrusion is positioned on the second layer such that it is above at least a part of the first and/or second molar teeth of the lower jaw. Similarly, when the appliance is fitted to the teeth on the upper jaw, the protrusion is positioned on the second layer such that it is below at least a part of the first and/or second molar teeth of the upper jaw. Accordingly, when reference is made herein to the appliance being fitted and the protrusion being positioned on the second layer such that it is over at least a part of the first and/or second teeth, this means that it is either above the first and/or second molar teeth of the lower jaw or below the first and/or second molar teeth of the upper jaw, depending upon which jaw it is fitted. The protrusion is preferably formed integrally with the second layer. Preferably, the protrusion is centrally located over at least a part of the first and/or second molar teeth. More preferably, the width of the protrusion is less than the width of the molar(s) over which the protrusion is intended to be positioned. The shape of the protrusion is not important, provided that in use it is comfortable for the patient and when the appliance is fitted the protrusion provides a point above/below the first and/or second molars on the lower/upper jaw about which the lower jaw may pivot, if forced to do so.

In one embodiment, the appliance of the present invention is suitable for use in a method of reducing facial aging and/or oral parafunctional activity, which method comprises fitting an appliance of the first aspect of the present invention in the mouth on either the upper or lower jaw, preferably the lower jaw, and exercising the lower jaw by repeatedly dropping the lower jaw and then lifting the lower jaw and closing it against the upper jaw with the appliance between the teeth. Exercising may be undertaken when the patient is conscious or asleep. Exercising may take place actively, for example during eating or at a time when the patient deliberately exercises. Alternatively, exercising may take place passively, for example when the patient is asleep or simply performing normal daytime activities. In such passive exercise, the facial muscles are stretched by the jaw adopting a new resting position. Exercising is preferably achieved by wearing the appliance continuously for from about 3 to about 12 hours in any day (it is recommended not to wear the appliance for 24 hours of the day). Exercising is preferably undertaken on a daily basis over a period of from 4 to 10 weeks, typically 6 weeks. A break from exercising of from 3 to 6 months e.g. 4 months is preferably taken before commencing another period of exercising.

In another embodiment, the appliance of the first aspect of the present invention is suitable for use in a method of reducing facial aging and/or oral parafunctional activity, which method comprises fitting an appliance of the invention in the mouth on either the upper or lower jaw, preferably the lower jaw, and over a period of five minutes, whilst keeping the lips together but with the jaws apart so that the top (or bottom) teeth do not touch the protrusions on the appliance, counting (or "ticking") the number of times the jaws close involuntarily, so causing the top (or bottom) teeth to touch the protrusions on the appliance. If, during this time, the patient suffers any pain, they should stop the exercise and remove the appliance from the mouth: three days later, the patient should wear the appliance for only half the time, and then build up to 5 minutes. Over time, as patient learns to relax with the appliance in their mouth, the patient should be able to reduce the number of involuntary jaw closures over the 5 minute period to zero without experiencing pain. Thus, in yet a further aspect of the present invention, there is provided a method for reducing facial aging and/or oral parafunctional activity in an individual, which method comprises fitting an appliance of the first aspect over at least two of the posterior teeth on both sides of either the upper jaw or lower jaw of an individual, closing the lips and, over a specified period of time, attempting to prevent involuntary jaw closures sufficient to cause the upper or lower teeth, respectively, to contact the protrusions on the second layer of the appliance. Preferably, the method is repeated every third day. This aspect of the invention may be combined with an aspect described earlier, wherein in a method of reducing facial aging and/or reducing oral parafunctional activity, the appliance is worn by the patient for up to 1 hour, twice a day, every third day and not at night time and not for eating. In this combined embodiment, at some point during the period (e.g. 1 hour) of wearing the appliance, the patient attempts to prevent said involuntary jaw closures for 5 minutes.

In the method of making the appliance of the present invention, the uncured rubber composition is preferably applied to the first surface of the second layer to provide a layer of uncured rubber that is preferably from 5 to 15 mm thick, more preferably 8 to 12 mm thick. After moulding of the uncured rubber composition, including optionally around orifices and/or projections of the second layer, and relevant teeth of the patient, the thickness of the layer will vary from point to point along the length of the appliance. Preferably, after moulding, the thickness of the first layer does not go below 1 mm. Once the uncured rubber composition has been moulded to the required shape, the thickness of the first layer does not change during or after curing.

It is the employment of an uncured rubber the first layer material in the composite structure of the appliance that enables the appliance during moulding to adjust to provide a vertical separation of the jaws determined by the command swallow technique.

The second layer of the appliance is formed from a durable, non-deformable material having a softening point over 100° C., e.g. 150° C. or more. Such materials are well known in the art and are commonly used in the manufacture of boil and bite type dental products, such as those described in U.S. Pat. Nos. 6,092,253, 6,415,794 and 6,539,943. Examples of suitable materials include polycarbonate resins, high density polyethylene and polypropylene and methylmethacrylate based thermoplastics. Commercially available materials include Escorene HD-6706 available from Exxon and AP6112-HS available from Huntsman. The material used to make the second layer must not become softened in boiling water.

The second layer is preferably from about 1 to about 15 mm thick, preferably from about 3 to about 9 mm thick. The thickness of the second layer is not affected by fitting. The second layer is provided with a protrusion formed of durable, non-deformable material having a softening point over 100° C. which extends from at least about 2 mm up to about 20 mm, preferably from about 5 mm up to about 15 mm, most preferably from about 7 mm to about 10 mm e.g. 9 mm, from the second surface of the second layer away from the first surface and which is positioned such that in use it is on the second layer over at least a part of the first and/or second molar teeth which are in contact with the first layer.

The cured rubber composition that forms the first layer tends to adhere itself to the first surface of the second layer during application and cure. If it is considered necessary to more securely contact the first layer to the second layer, the second layer of each part is preferably provided with a plurality of orifices and/or projections into which or around which the first layer is moulded.

The appliance may comprise a third layer of material located between the first and second layers. If present, such a third layer is preferably formed of a durable resilient material having a softening point above 100° C., preferably above 150° C. Such suitable materials are mentioned above.

The protrusion is preferably formed out of the same material as the second layer and is preferably formed integrally with the second layer. Together, the protrusion and second layer are preferably no more than 22 mm thick at their thickest point, more preferably no more than 15 mm thick at their thickest point.

The appliance of the present invention can be fitted to a patient by a method that includes the use of the command swallow technique during the moulding of the first layer.

The appliance of the present invention is useful for reducing facial aging. The aging of the face basically involves two factors. These are intrinsic and extrinsic factors. The intrinsic factors basically involve atrophy i.e. the reduction in number of cells for instance by the age of 60 (typically, we only have 60% of the muscle cells that we had when we were in our 20's). The extrinsic factors involve damage done to cells by environmental factors e.g. sun, smoke, toxins produced by bacteria and viruses. The process involved is basically a form of chronic inflammation. Both these processes (cell death and chronic inflammation) in their early stages are reversible. Exercising with the appliance of the present invention can help reverse these processes in their early stages. Accordingly, all diseases, which are related to facial aging or inflammatory conditions, could be alleviated to some extent by exercising with the appliance. For example, exercising with the appliance could help to alleviate, to some extent, some of the symptoms associated with suffers of Alzheimer's, chronic sinusitis, age related deterioration in eyesight, tangelacetasis, solar damage to the skin, acne, and bacterial infections, such as ear infections. This list is not exhaustive.

BRIEF DESCRIPTION OF THE DRAWINGS

The invention in its various embodiments shall now be further described by way of exemplification with reference to the accompanying drawings, in which.

DETAILED DESCRIPTION

Figure 1:
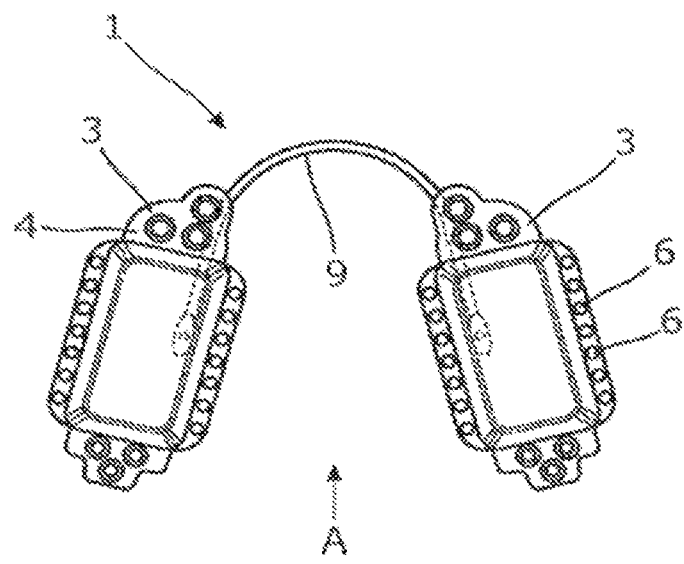
FIG. 1 is a plan view from above of an appliance-preform.
Figure 2:
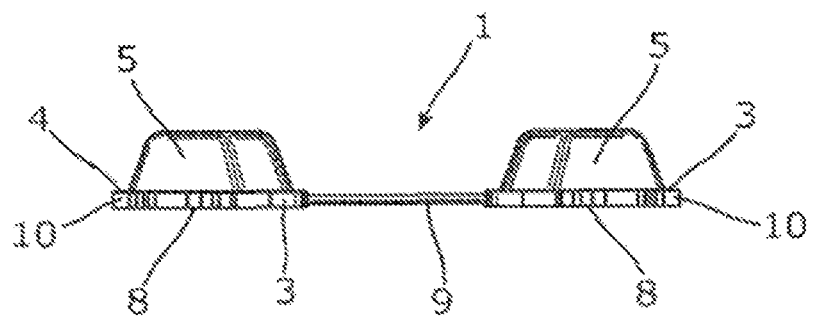
FIG. 2 is a side view of the appliance-preform shown in FIG. 1 from position A.
Figure 3:
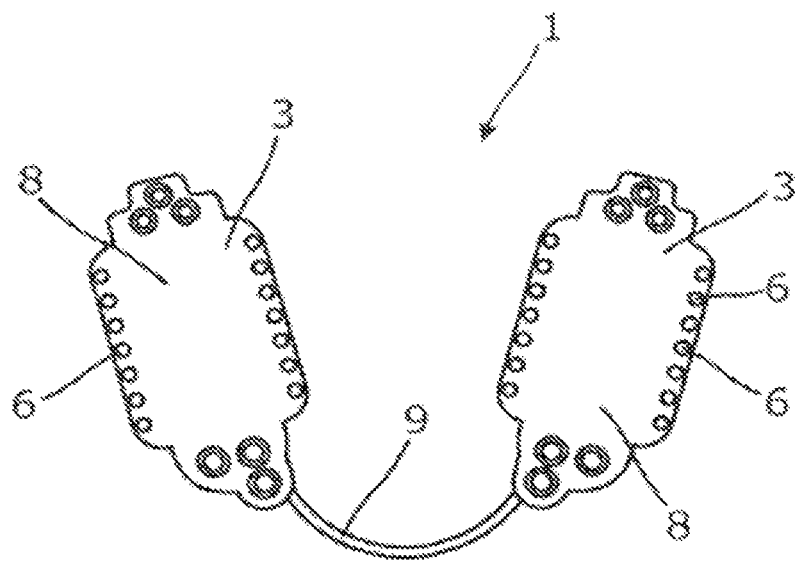
FIG. 3 is a plan view from below of the appliance-preform shown in FIG. 1.
Figure 4:
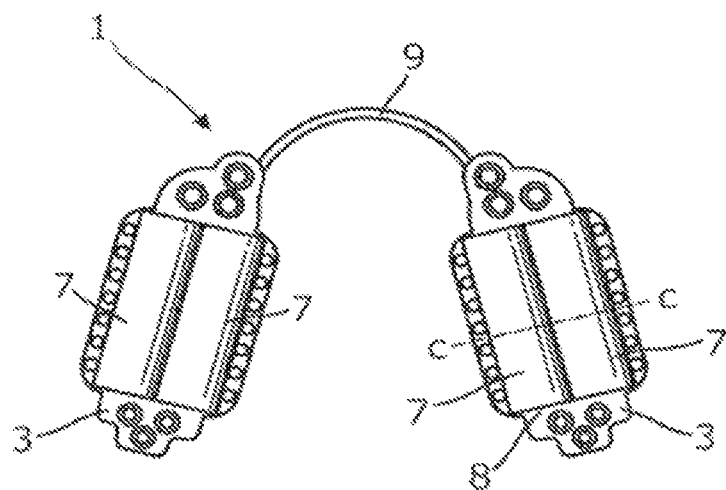
FIG. 4 is a plan view from below of the appliance-preform shown in FIG. 1 after two strips of uncured rubber have been applied (i.e. after step iii) of the second aspect of the present invention).
Figure 5:
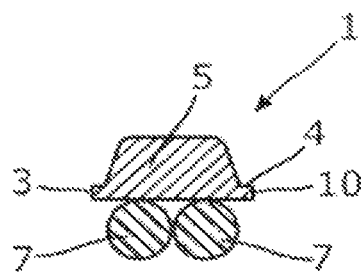
FIG. 5 is a cross-sectional view along the line c-c of the embodiment shown in FIG. 4.

An appliance-preform 1, as shown in FIGS. 1-6, comprises two second layers 3, each about 1.5 mm thick formed of a commercially available substantially transparent polycarbonate having a softening point of about 190° C., having a first surface 8, a second surface 4 and walls 10 between said surfaces that define their borders. The second layer 3 forms, in use, a bite plate. Extending from the second surface 4, away from the first surface 8, is a protrusion 5 which is formed integrally with the second layer 3. The protrusion extends approximately 3 mm above the second surface 4. The substantially planar first surface 8 of the second layer 3 contacts two strips of uncured rubber composition 7, as shown in FIGS. 4 and 5, which have been applied to the first surface 8 and which after curing provide a first layer 2. A stainless steel wire 9, which in another embodiment may be a plastic strip, forms a bridging means between the two second layers 3.

Figure 6:
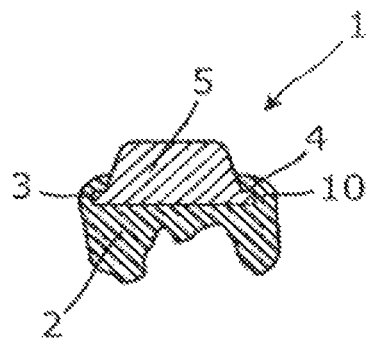
FIG. 6 is a cross-sectional view along the line c-c of the embodiment shown in FIG. 4 but after the two strips of uncured rubber composition have been moulded to the patient's teeth and second layer and cured (i.e. after steps iv) v) of the second aspect of the present invention).

The second layer 3 is provided with a plurality small orifices 6 into which, as shown in FIG. 6, the first layer 2, formed after moulding and curing of the uncured rubber strips 7, engages to secure itself to the second layer 3.

The appliance-preform and two strips of uncured rubber 7, as shown in FIGS. 4 and 5, can be fitted to a patient by a method in which the patient is required to open the mouth and the uncured rubber is then placed over the teeth on the patient's lower jaw, with the uncured rubber in contact with the teeth and the protrusion 5 positioned over both first molar teeth. The patient is then required to gently raise the lower jaw until the teeth on the upper jaw contact the top of the protrusion 5. The patient then closes their lips and swallows. The pressure applied to the appliance-preform and uncured rubber composition by swallowing causes the uncured rubber composition to deform and mould itself to the shape of the teeth on the lower jaw and into and around the orifices 6 in the second layer 3. The appliance can then be carefully removed from the mouth of the patient left overnight at ambient temperature for the uncured rubber to cure. Once the rubber composition has cured, any excess rubber composition can be trimmed away with a knife or razor blade until it forms a comfortable fit in the patient's mouth.

The fitting of the appliance can readily be performed by a doctor or dentist, without the services of a dental technician or having to resort to custom moulding practices in a laboratory, or by the patient without third party assistance.

Once the uncured rubber composition has cured and any excess trimmed away, the appliance of the invention may be used by the patient for reducing facial aging.

The process for reducing facial aging and/or oral parafunctional activity can commence as soon as the uncured rubber has cured and any excess trimmed away.

In one embodiment, the patient positions the appliance of the invention in the mouth, preferably just before eating a meal. The patient then exercises the lower jaw, e.g. during eating or sleeping, by raising the lower jaw thereby to bring the teeth on the upper jaw into contact with the protrusions and then closing the teeth on the upper and lower jaw around the appliance. In so doing, the lower jaw is forced to pivot slightly about the protections and cause the facial muscles controlling the lower jaw to work harder. The muscles are then permitted to relax and the lower jaw is dropped. The exercise is preferably repeated for about 6 to 7 hours a day over a period of about 6 weeks.

The appliance-preform may be packaged as a kit of parts together with either a single pack composition, comprising an uncured rubber composition, e.g. in a syringe or blister pack, or a two-pack composition, comprising two compositions that when mixed together form an uncured rubber composition, and optionally with a set of instructions for making an appliance of the present invention.

The invention claimed is:

1. An appliance comprising two parts, the two parts intended in use to contact at least first and/or second molar teeth on respective opposite sides of either upper or lower jaw, each of the two parts comprising a composite structure comprising:
    a first component comprising a durable and resilient first layer formed of an ambient-temperature-cured thermoset rubber composition, which in use contacts at least occlusal biting surfaces of the first and/or second molar teeth; and
    a second component comprising a body with a first surface, a second surface opposite the first surface and one or more side walls extending between the first surface and the second surface, wherein the first surface is substantially planar and comprises a solid support area, the second component comprising a protrusion extending from the second surface, wherein the solid support area is configured to receive the occlusal biting surfaces of the first and/or second molar teeth,
    wherein the first component after moulding and curing extends around the second component and contacts portions of the solid support area, the one or more side walls and the second surface, thereby securing the first component to the second component,
    wherein the second component is formed of a durable, non-deformable material having a softening point over 100° C., and which in use provides a bite plate,
    wherein the protrusion extends from at least 2 mm up to 20 mm from said second surface away from the first layer; and
    wherein the one or more side walls that border said first and second surfaces do not extend from said first surface in a direction away from said second surface.

2. The appliance of claim 1, wherein said ambient-temperature-cured, thermoset rubber composition comprises a cured silicone rubber.

3. A method for making an appliance, wherein said appliance comprises two parts, the two parts intended in use to contact at least first and/or second molar teeth on respective opposite sides of either upper or lower jaw, each of the two parts comprising a composite structure comprising:
    a first component comprising a durable and resilient first layer formed of an ambient-temperature-cured thermoset rubber composition, which in use contacts at least occlusal biting surfaces of the first and/or second molar teeth; and
    a second component comprising a body with a first surface, a second surface opposite the first surface and one or more side walls extending between the first surface and the second surface, wherein the first surface is substantially planar and comprises a solid support area, the second component comprising a protrusion extending from the second surface, wherein the solid support area is configured to receive the occlusal biting surfaces of the first and/or second molar teeth,
    wherein the second component is formed of a durable, non-deformable material having a softening point over 100° C., and which in use provides a bite plate,
    wherein the protrusion extends from at least 2 mm up to 20 mm from said second surface away from the first layer; and
        wherein the one or more side walls that border said first and second surfaces do not extend from said first surface in a direction away from said second surface;
    wherein said method comprises:
    i) providing an appliance-preform comprising two second components;
    ii) providing an uncured rubber composition which at ambient temperature cures to form the ambient-temperature-cured thermoset rubber composition of the first layer;
    iii) applying said uncured rubber composition on to said first surface of each of said second components;

iv) moulding the uncured rubber composition into a shape of the at least occlusal biting surfaces of the first and/or second molar teeth and to extend around the second component and contact portions of the solid support area, the one or more side walls and the second surface; and v) curing said moulded uncured rubber composition at ambient temperature, thereby forming the ambient-temperature-cured thermoset rubber composition of the first layer and securing first layer to the second component.

4. A kit for making an appliance, wherein said appliance comprises two parts, the two parts intended in use to contact at least first and/or second molar teeth on respective opposite sides of either upper or lower jaw, each of the two parts comprising a composite structure comprising:

a first component comprising a durable and resilient first layer formed of an ambient-temperature-cured thermoset rubber composition, which in use contacts at least occlusal biting surfaces of the first and/or second molar teeth; and a second component comprising a body with a first surface, a second surface opposite the first surface and one or more side walls extending between the first surface and the second surface, wherein the first surface is substantially planar and comprises a solid support area, the second component comprising a protrusion extending from the second surface, wherein the solid support area is configured to receive the occlusal biting surfaces of the first and/or second molar teeth, wherein the first component after moulding and curing extends around the second component and contacts portions of the solid support area, the one or more side walls and the second surface, thereby securing the first component to the second component, wherein the second component is formed of a durable, non-deformable material having a softening point over 100° C., and which in use provides a bite plate, wherein the protrusion extends from at least 2 mm up to 20 mm from the second surface away from the first layer; and wherein the one or more side walls that border said first and second surfaces do not extend from said first surface in a direction away from said second surface;

wherein said kit comprises:

a) an appliance-preform comprising two second components; and b) an uncured rubber composition which at ambient temperature cures to form the ambient-temperature-cured thermoset rubber composition of the first layer, or a multipack composition comprising at least two components that when mixed together form the ambient-temperature-cured thermoset rubber composition of the first layer.

5. The kit of claim 4, further comprising instructions for making the appliance.

6. The method of claim 3, wherein said uncured rubber composition comprises a silicone rubber.

7. A method for reducing facial aging and/or oral parafunctional activity in an individual, comprising:

providing an appliance comprising two parts, the two parts intended in use to contact at least first and/or second molar teeth on respective opposite sides of either upper or lower jaw, each of the two parts comprising a composite structure comprising:

a first component comprising a durable and resilient first layer formed of an ambient-temperature-cured thermoset rubber composition, which in use contacts at least occlusal biting surfaces of the first and/or second molar teeth; and a second component comprising a body with a first surface, a second surface opposite the first surface and one or more side walls extending between the first surface and the second surface, wherein the first surface is substantially planar and comprises a solid support area, the second component comprising a protrusion extending from the second surface, wherein the solid support area is configured to receive the occlusal biting surfaces of the first and/or second molar teeth, wherein the first component after moulding and curing extends around the second component and contacts portions of the solid support area, the one or more side walls and the second surface, thereby securing the first component to the second component, wherein the second component is formed of a durable, non-deformable material having a softening point over 100° C., and which in use provides a bite plate, wherein the protrusion extends from at least 2 mm up to 20 mm from said second surface away from the first layer; and wherein the one or more side walls that border said first and second surfaces do not extend from said first surface in a direction away from said second surface; and fitting the appliance over at least two posterior teeth, including at least one of the at least first and/or second molar teeth on both sides of either the upper jaw or lower jaw of the individual, wherein the occlusal biting surfaces of the first and/or second molar teeth are in contact with the first layer of each of the two parts of the appliance, closing lips of the individual, and, over a specified period of time, the individual attempting to prevent involuntary jaw closures sufficient to cause upper or lower teeth to contact the protrusion of each of the two parts on the second component of the appliance.

8. The method of claim 7, wherein said method is repeated every third day.

9. The method of claim 7, wherein said specified period of time is 5 minutes.

10. A method of reducing facial aging and/or reducing oral parafunctional activity in an individual, comprising:

providing an appliance comprising two parts, the two parts intended in use to contact at least first and/or second molar teeth on respective opposite sides of either upper or lower jaw, each of the two parts comprising a composite structure comprising:

a first component comprising a durable and resilient first layer formed of an ambient-temperature-cured thermoset rubber composition, which in use contacts at least occlusal biting surfaces of the first and/or second molar teeth; and a second component comprising a body with a first surface, a second surface opposite the first surface and one or more side walls extending between the first surface and the second surface, wherein the first surface is substantially planar and comprises a solid support area, the second component comprising a protrusion extending from the second surface, wherein the solid support area is configured to receive the occlusal biting surfaces of the first and/or second molar teeth, wherein the first component after moulding and curing extends around the second component and contacts portions of the solid support area, the one or more side walls and the second surface, thereby securing the first component to the second component, wherein the second component is formed of a durable, non-deformable material having a softening point over 100° C., and which in use provides a bite plate, wherein the protrusion extends from at least 2 mm up to 20 mm from said second surface away from the first layer; and wherein the one or more side walls that border said first and second surfaces do not extend from said first surface in a direction away from said second surface;

fitting the appliance over at least two posterior teeth, including at least one of the at least first and/or second molar teeth, on both sides of either the upper jaw or lower jaw of an individual, wherein the occlusal biting surfaces of the first and/or second molar teeth are in contact with the first layer of each of the two parts of the appliance, and wherein the appliance is worn by the individual for up to 1 hour, twice a day, every third day and not at nighttime and not while eating.

11. The method of claim 10, wherein at some point while the Individual is wearing the appliance, the individual closes their lips and, over a specified period of time, attempts to prevent involuntary jaw closures sufficient to cause the upper or lower teeth to contact the protrusion of each of the two parts on the second component of the appliance.

12. The appliance of claim 1, wherein the second component of each of the parts comprises a plurality of orifices into which or around which the first layer is moulded to secure the first layer to the second component.

13. A method for reducing facial aging and/or reducing oral parafunctional activity in an individual, comprising:
providing an appliance comprising two parts, the two parts intended in use to contact at least first and/or second molar teeth on respective opposite sides of either upper or lower jaw, each of the two parts comprising a composite structure comprising:
a first component comprising a durable and resilient first layer formed of an ambient-temperature-cured thermoset rubber composition, which in use contacts at least occlusal biting surfaces of the first and/or second molar teeth; and
a second component comprising a body with a first surface, a second surface opposite the first surface and one or more side walls extending between the first surface and the second surface, wherein the first surface is substantially planar and comprises a solid support area, the second component comprising a protrusion extending from the second surface, wherein the solid support area is configured to receive the occlusal biting surfaces of the first and/or second molar teeth,
wherein the second component is formed of a durable, non-deformable material having a softening point over 100° C., wherein the second component in use provides a bite plate, wherein the second component comprises a plurality of orifices,
wherein the first component after moulding and curing extends through the orifices in and around the second component, thereby securing the first component to the second component,
wherein the protrusion extends from at least 2 mm up to 20 mm from said second surface away from the first layer; and wherein the one or more side walls that border said first and second surfaces do not extend from said first surface in a direction away from said second surface; and fitting the appliance over at least two posterior teeth, including at least one of the first and/or second molar teeth, on both sides of either the upper jaw or lower jaw of an individual, wherein the occlusal biting surfaces of the first and/or second molar teeth are in contact with the first layer of each of the two parts of the appliance, closing the lips of the individual, and, over a specified period of time, the individual attempts to prevent involuntary jaw closures sufficient to cause upper or lower teeth to contact the protrusion of each of the two parts on the second component of the appliance.

14. The method of claim 13, wherein said specified period of time is 5 minutes.

15. A method of reducing facial aging and/or reducing oral parafunctional activity in an individual, comprising:
providing an appliance comprising two parts, the two parts intended in use to contact at least first and/or second molar teeth on respective opposite sides of either upper or lower jaw, each of the two parts comprising a composite structure comprising:
a first component comprising a durable and resilient first layer formed of an ambient-temperature-cured thermoset silicone rubber composition, which in use contacts at least occlusal biting surfaces of the first and/or second molar teeth; and
a second component comprising a body with a first surface, a second surface opposite the first surface and one or more side walls extending between the first surface and the second surface, wherein the first surface is substantially planar and comprises a solid support area, the second component comprising a protrusion extending from the second surface, wherein the solid support area is configured to receive the occlusal biting surfaces of the first and/or second molar teeth,
wherein the second component is a second layer formed of a durable, non-deformable material having a softening point over 100° C., and which in use provides a bite plate,
wherein the protrusion extends from at least 2 mm up to 20 mm from said second surface away from the first layer;
wherein the one or more side walls that border said first and second surfaces do not extend from said first surface in a direction away from said second surface; and
wherein the first component after moulding and curing extends around the second component and contacts portions of the solid support area, the one or more side walls and the second surface, thereby securing the first component to the second component,
the method comprising:
fitting the appliance over at least two posterior teeth, including at least one of the first and/or second molar teeth, on both sides of the upper jaw or lower jaw of an individual,
wherein the occlusal biting surfaces of the first and/or second molar teeth are in contact with the first layer of each of the two parts of the appliance, and
wherein the appliance is worn by the individual for up to 1 hour, twice a day, every third day and not a nighttime and not while eating.

16. The method of claim 3, wherein the second component of each of the two parts comprises a plurality of orifices into which the first layer is moulded to secure the first layer to the second component.

17. The kit of claim 4, wherein the second component of each of the two parts comprises a plurality of orifices into which the first layer can be moulded to secure the first layer to the second component.

18. The appliance of claim 1, wherein the two parts are joined by a plastic strip or stainless steel wire.

19. The kit of claim 4, wherein said ambient-temperature-cured, thermoset rubber composition comprises a cured silicone rubber.

* * * * *